United States Defensive Publication [19] (H) [11] T983,009

Treat [43] Jun. 5, 1979

[54] PROCESS FOR REMOVING TOXIC PERFLUOROISOBUTYLENE

[75] Inventor: Theodore A. Treat, Washington, W. Va.

[73] Assignee: E. I. DuPont de Nemours and Company, Wilmington, Del.

[21] Appl. No.: 960,013

[22] Filed: Nov. 13, 1978

Related U.S. Application Data

[63] Continuation of Ser. No. 850,221, Nov. 10, 1977, abandoned.

[51] Int. Cl.[2] ..... C07C 19/00

[52] U.S. Cl. ..... 260/652 P

[57] ABSTRACT

A process for converting toxic perfluoroisobutylene in a mixture of fluorine-containing compounds into a relatively nontoxic ether which comprises contacting the mixture with a solution of methanol and a selected hydrogen halide.

5 Claims, No Sheets Drawing,

9 Pages Specification

The file of this unexamined application may be inspected and copies thereof may be purchased (849 O.G. 1221, Apr. 9, 1968).